US011517719B2

United States Patent
Howell

(10) Patent No.: US 11,517,719 B2
(45) Date of Patent: Dec. 6, 2022

(54) INTEGRATED ACUTE CENTRAL VENOUS CATHETER AND PERIPHERALLY INSERTED VENOUS CATHETER

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

(*) Notice: Subject to any disclaimer, the term of this patent is extended or adjusted under 35 U.S.C. 154(b) by 168 days.

(21) Appl. No.: 17/031,478

(22) Filed: Sep. 24, 2020

(65) Prior Publication Data

US 2021/0085927 A1  Mar. 25, 2021

Related U.S. Application Data

(60) Provisional application No. 62/905,363, filed on Sep. 24, 2019.

(51) Int. Cl.
*A61M 25/06* (2006.01)
*A61M 25/09* (2006.01)
(Continued)

(52) U.S. Cl.
CPC ........ *A61M 25/06* (2013.01); *A61M 25/0097* (2013.01); *A61M 25/02* (2013.01);
(Continued)

(58) Field of Classification Search
CPC .............. A61M 25/0606; A61M 25/06; A61M 25/0097; A61M 25/09; A61M 2039/064;
(Continued)

(56) References Cited

U.S. PATENT DOCUMENTS 1,013,691 A  1/1912  Shields
3,225,762 A  12/1965 Guttman
(Continued)

FOREIGN PATENT DOCUMENTS

DE  202012006191 U1  7/2012
EP  0730880 A1  9/1996
(Continued)

OTHER PUBLICATIONS

PCT/US2021/014700 filed Jan. 22, 2021 International Search Report and Written Opinion dated Jun. 29, 2021.
(Continued)

*Primary Examiner* — Bhisma Mehta
*Assistant Examiner* — Phoebe Anne Staton
(74) *Attorney, Agent, or Firm* — Rutan & Tucker LLP

(57) ABSTRACT

A catheter assembly includes a peripheral intravenous ("PIV") portion that provides expedited vascular access. The catheter assembly includes an elongate catheter body defining a first lumen and includes a CVC portion, a transition portion, and a PIV portion. The PIV portion defines a relatively smaller diameter, a tapered tip, and a lumen configured to receive a needle. The needle extends through a needle access aperture, disposed through a side wall of the catheter body, through the PIV lumen, to a point beyond a distal end of the catheter body. A clinician accesses a vasculature using the needle and the PIV portion. The needle is then removed and a guidewire advanced through the lumen of the catheter body and the PIV portion into the vasculature. The CVC portion is then advanced over the guidewire into the vasculature, self-dilating the insertion site as the transition portion enters the vasculature.

23 Claims, 5 Drawing Sheets

(51) Int. Cl.
  *A61M 39/06* (2006.01)
  *A61M 25/00* (2006.01)
  *A61M 39/24* (2006.01)
  *A61M 25/02* (2006.01)

(52) U.S. Cl.
  CPC ........ *A61M 25/0606* (2013.01); *A61M 25/09* (2013.01); *A61M 39/24* (2013.01); *A61M 2025/024* (2013.01); *A61M 2039/064* (2013.01); *A61M 2039/2426* (2013.01)

(58) Field of Classification Search
  CPC ........ A61M 2025/024; A61M 25/0631; A61M 25/0662; A61M 25/0169; A61M 25/0172; A61M 2025/0177; A61M 25/0693; A61B 17/3439
  See application file for complete search history.

(56) References Cited

U.S. PATENT DOCUMENTS

| | | |
|---|---|---|
| 3,382,872 A | 5/1968 | Rubin |
| 3,570,485 A | 3/1971 | Reilly |
| 3,890,976 A | 6/1975 | Bazell et al. |
| 4,205,675 A | 6/1980 | Vaillancourt |
| 4,292,970 A | 10/1981 | Hession, Jr. |
| 4,468,224 A | 8/1984 | Enzmann et al. |
| 4,525,157 A | 6/1985 | Vaillancourt |
| 4,581,019 A | 4/1986 | Curelaru et al. |
| 4,594,073 A | 6/1986 | Stine |
| 4,702,735 A | 10/1987 | Luther et al. |
| 4,743,265 A | 5/1988 | Whitehouse et al. |
| 4,766,908 A | 8/1988 | Clement |
| 4,863,432 A | 9/1989 | Kvalo |
| 4,994,040 A | 2/1991 | Cameron et al. |
| 5,017,259 A | 5/1991 | Kohsai |
| 5,040,548 A | 8/1991 | Yock |
| 5,057,073 A | 10/1991 | Martin |
| 5,112,312 A | 5/1992 | Luther |
| 5,115,816 A | 5/1992 | Lee |
| 5,120,317 A | 6/1992 | Luther |
| 5,188,593 A | 2/1993 | Martin |
| 5,195,962 A | 3/1993 | Martin et al. |
| 5,207,650 A | 5/1993 | Martin |
| 5,267,958 A | 12/1993 | Buchbinder et al. |
| 5,295,970 A | 3/1994 | Clinton et al. |
| 5,306,247 A | 4/1994 | Pfenninger |
| 5,322,512 A | 6/1994 | Mohiuddin |
| 5,328,472 A | 7/1994 | Steinke et al. |
| 5,350,358 A | 9/1994 | Martin |
| 5,368,567 A | 11/1994 | Lee |
| 5,378,230 A | 1/1995 | Mahurkar |
| 5,380,290 A | 1/1995 | Makower et al. |
| 5,389,087 A | 2/1995 | Miraki |
| 5,439,449 A | 8/1995 | Mapes et al. |
| 5,443,457 A | 8/1995 | Ginn et al. |
| 5,489,271 A | 2/1996 | Andersen |
| 5,573,520 A | 11/1996 | Schwartz et al. |
| 5,683,370 A | 11/1997 | Luther et al. |
| 5,718,678 A | 2/1998 | Fleming, III |
| 5,772,636 A | 6/1998 | Brimhall et al. |
| 5,885,251 A | 3/1999 | Luther |
| 5,919,164 A | 7/1999 | Andersen |
| 5,947,940 A | 9/1999 | Beisel |
| 5,957,893 A | 9/1999 | Luther et al. |
| 6,206,849 B1 | 3/2001 | Martin et al. |
| 6,475,187 B1 | 11/2002 | Gerberding |
| 6,606,515 B1 | 8/2003 | Windheuser et al. |
| 6,716,228 B2 | 4/2004 | Tal |
| 6,726,659 B1 | 4/2004 | Stocking et al. |
| 6,819,951 B2 | 11/2004 | Patel et al. |
| 6,821,287 B1 | 11/2004 | Jang |
| 6,926,692 B2 | 8/2005 | Katoh et al. |
| 6,962,575 B2 | 11/2005 | Tal |
| 6,991,625 B1 | 1/2006 | Gately et al. |
| 6,994,693 B2 | 2/2006 | Tal |
| 6,999,809 B2 | 2/2006 | Currier et al. |
| 7,025,746 B2 | 4/2006 | Tal |
| 7,029,467 B2 | 4/2006 | Currier et al. |
| 7,037,293 B2 | 5/2006 | Carrillo et al. |
| 7,074,231 B2 | 7/2006 | Jang |
| 7,141,050 B2 | 11/2006 | Deal et al. |
| 7,144,386 B2 | 12/2006 | Korkor et al. |
| 7,311,697 B2 | 12/2007 | Osborne |
| 7,364,566 B2 | 4/2008 | Elkins et al. |
| 7,377,910 B2 | 5/2008 | Katoh et al. |
| 7,390,323 B2 | 6/2008 | Jang |
| D600,793 S | 9/2009 | Bierman et al. |
| D601,242 S | 9/2009 | Bierman et al. |
| D601,243 S | 9/2009 | Bierman et al. |
| 7,594,911 B2 | 9/2009 | Powers et al. |
| 7,691,093 B2 | 4/2010 | Brimhall |
| 7,722,567 B2 | 5/2010 | Tal |
| D617,893 S | 6/2010 | Bierman et al. |
| D624,643 S | 9/2010 | Bierman et al. |
| 7,819,889 B2 | 10/2010 | Healy et al. |
| 7,857,788 B2 | 12/2010 | Racz |
| D630,729 S | 1/2011 | Bierman et al. |
| 7,909,797 B2 | 3/2011 | Kennedy, II et al. |
| 7,909,811 B2 | 3/2011 | Agro et al. |
| 7,922,696 B2 | 4/2011 | Tal et al. |
| 7,938,820 B2 | 5/2011 | Webster et al. |
| 7,967,834 B2 | 6/2011 | Tal et al. |
| 7,976,511 B2 | 7/2011 | Fojtik |
| 7,985,204 B2 | 7/2011 | Katoh et al. |
| 8,073,517 B1 | 12/2011 | Burchman |
| 8,105,286 B2 | 1/2012 | Anderson et al. |
| 8,192,402 B2 | 6/2012 | Anderson et al. |
| 8,202,251 B2 | 6/2012 | Bierman et al. |
| 8,206,356 B2 | 6/2012 | Katoh et al. |
| 8,372,107 B2 | 2/2013 | Tupper |
| 8,377,006 B2 | 2/2013 | Tal et al. |
| 8,454,577 B2 | 6/2013 | Joergensen et al. |
| 8,585,858 B2 | 11/2013 | Kronfeld et al. |
| 8,657,790 B2 | 2/2014 | Tal et al. |
| 8,672,888 B2 | 3/2014 | Tal |
| 8,696,645 B2 | 4/2014 | Tal et al. |
| 8,784,362 B2 | 7/2014 | Boutilette et al. |
| 8,827,958 B2 | 9/2014 | Bierman et al. |
| 8,876,704 B2 | 11/2014 | Golden et al. |
| 8,882,713 B1 | 11/2014 | Call et al. |
| 8,900,192 B2 | 12/2014 | Anderson et al. |
| 8,900,207 B2 | 12/2014 | Uretsky |
| 8,915,884 B2 | 12/2014 | Tal et al. |
| 8,956,327 B2 | 2/2015 | Bierman et al. |
| 9,023,093 B2 | 5/2015 | Pal |
| 9,138,252 B2 | 9/2015 | Bierman et al. |
| 9,180,275 B2 | 11/2015 | Helm |
| 9,265,920 B2 | 2/2016 | Rundquist et al. |
| 9,272,121 B2 | 3/2016 | Piccagli |
| 9,522,254 B2 | 12/2016 | Belson |
| 9,554,785 B2 | 1/2017 | Walters et al. |
| 9,566,087 B2 | 2/2017 | Bierman et al. |
| 9,675,784 B2 | 6/2017 | Belson |
| 9,713,695 B2 | 7/2017 | Bunch et al. |
| 9,764,117 B2 | 9/2017 | Bierman et al. |
| 9,770,573 B2 | 9/2017 | Golden et al. |
| 9,814,861 B2 | 11/2017 | Boutilette et al. |
| 9,820,845 B2 | 11/2017 | von Lehe et al. |
| 9,861,383 B2 | 1/2018 | Clark |
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 | 3/2018 | Tal et al. |
| 9,981,113 B2 | 5/2018 | Bierman |
| 10,010,312 B2 | 7/2018 | Tegels |
| 10,065,020 B2 | 9/2018 | Gaur |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |

(56) References Cited

U.S. PATENT DOCUMENTS

| | | |
|---|---|---|
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,806,901 B2 | 10/2020 | Burkholz et al. |
| 2002/0040231 A1 | 4/2002 | Wysoki |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0015138 A1 | 1/2004 | Currier et al. |
| 2004/0116901 A1 | 6/2004 | Appling |
| 2004/0167478 A1* | 8/2004 | Mooney ............ A61M 25/0097 604/264 |
| 2004/0193093 A1 | 9/2004 | Desmond |
| 2004/0230178 A1 | 11/2004 | Wu |
| 2005/0004554 A1 | 1/2005 | Osborne |
| 2005/0215956 A1 | 9/2005 | Nerney |
| 2005/0245882 A1 | 11/2005 | Elkins et al. |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2008/0045894 A1 | 2/2008 | Perchik et al. |
| 2008/0125744 A1 | 5/2008 | Treacy |
| 2008/0125748 A1 | 5/2008 | Patel |
| 2008/0132850 A1 | 6/2008 | Fumiyama et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2009/0221961 A1 | 9/2009 | Tal et al. |
| 2009/0270889 A1 | 10/2009 | Tal et al. |
| 2010/0256487 A1 | 10/2010 | Hawkins et al. |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0144620 A1 | 6/2011 | Tal |
| 2011/0152836 A1 | 6/2011 | Riopelle et al. |
| 2011/0202006 A1* | 8/2011 | Bierman ............ A61M 25/0606 604/164.03 |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0220942 A1 | 8/2012 | Hall et al. |
| 2012/0283640 A1 | 11/2012 | Anderson et al. |
| 2012/0316500 A1 | 12/2012 | Bierman et al. |
| 2013/0053763 A1 | 2/2013 | Makino et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0100552 A1 | 4/2014 | Gallacher et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0080939 A1 | 3/2015 | Adams et al. |
| 2015/0112310 A1* | 4/2015 | Call ..................... A61M 39/10 604/528 |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0320977 A1 | 11/2015 | Vitullo et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Bamell |
| 2016/0114124 A1 | 4/2016 | Tal |
| 2016/0220786 A1 | 8/2016 | Mitchell et al. |
| 2016/0325073 A1 | 11/2016 | Davies et al. |
| 2016/0338728 A1 | 11/2016 | Tal |
| 2016/0346503 A1 | 12/2016 | Jackson et al. |
| 2017/0035990 A1 | 2/2017 | Swift |
| 2017/0072165 A1 | 3/2017 | Lim et al. |
| 2017/0128700 A1 | 5/2017 | Roche Rebollo |
| 2017/0172653 A1 | 6/2017 | Urbanski et al. |
| 2017/0239443 A1 | 8/2017 | Abitabilo et al. |
| 2017/0273713 A1 | 9/2017 | Shah et al. |
| 2017/0326339 A1 | 11/2017 | Bailey et al. |
| 2017/0361070 A1 | 12/2017 | Hivert |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0214674 A1* | 8/2018 | Ebnet ................ A61M 25/0606 |
| 2018/0296799 A1 | 10/2018 | Horst et al. |
| 2018/0296804 A1 | 10/2018 | Bierman |
| 2019/0015646 A1 | 1/2019 | Matlock et al. |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0255294 A1 | 8/2019 | Mitchell et al. |
| 2019/0275303 A1 | 9/2019 | Tran et al. |
| 2019/0276268 A1 | 9/2019 | Akingba |
| 2019/0321590 A1 | 10/2019 | Burkholz et al. |
| 2020/0016374 A1 | 1/2020 | Burkholz et al. |
| 2020/0237278 A1 | 7/2020 | Asbaghi |
| 2021/0069471 A1 | 3/2021 | Howell |
| 2021/0085927 A1 | 3/2021 | Howell |
| 2021/0100985 A1* | 4/2021 | Akcay ............... A61M 25/0618 |
| 2021/0113809 A1 | 4/2021 | Howell |
| 2021/0113810 A1 | 4/2021 | Howell |
| 2021/0121661 A1 | 4/2021 | Howell |
| 2021/0121667 A1 | 4/2021 | Howell |
| 2021/0228843 A1 | 7/2021 | Howell et al. |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001138 A1 | 1/2022 | Howell |
| 2022/0032013 A1 | 2/2022 | Howell et al. |
| 2022/0032014 A1 | 2/2022 | Howell et al. |
| 2022/0062528 A1 | 3/2022 | Thornley et al. |
| 2022/0126064 A1 | 4/2022 | Tobin et al. |
| 2022/0193376 A1 | 6/2022 | Spataro et al. |
| 2022/0193377 A1 | 6/2022 | Haymond et al. |
| 2022/0193378 A1 | 6/2022 | Spataro et al. |

FOREIGN PATENT DOCUMENTS

| | | |
|---|---|---|
| EP | 2061385 A1 | 5/2009 |
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |

(56) References Cited

FOREIGN PATENT DOCUMENTS

| | | |
|---|---|---|
| EP | 2486951 A2 | 8/2012 |
| EP | 2512576 A2 | 10/2012 |
| EP | 2152348 B1 | 2/2015 |
| EP | 3093038 B1 | 5/2019 |
| EP | 2260897 B1 | 9/2019 |
| GB | 1273547 A | 5/1972 |
| WO | 94/21315 A1 | 9/1994 |
| WO | 95/32009 A2 | 11/1995 |
| WO | 98/44979 A1 | 10/1998 |
| WO | 98/53871 A1 | 12/1998 |
| WO | 99/12600 A1 | 3/1999 |
| WO | 99/26681 A1 | 6/1999 |
| WO | 00/06221 A1 | 2/2000 |
| WO | 2003008020 A1 | 1/2003 |
| WO | 2003057272 A2 | 7/2003 |
| WO | 03/068073 A1 | 8/2003 |
| WO | 2003066125 A2 | 8/2003 |
| WO | 2006055288 A2 | 5/2006 |
| WO | 2006055780 A2 | 5/2006 |
| WO | 2007046850 A2 | 4/2007 |
| WO | 2008033983 A1 | 3/2008 |
| WO | 2008092029 A2 | 7/2008 |
| WO | 2008/131300 A2 | 10/2008 |
| WO | 2008131289 A2 | 10/2008 |
| WO | 2009114833 A1 | 9/2009 |
| WO | 2009114837 A2 | 9/2009 |
| WO | 2010/048449 A2 | 4/2010 |
| WO | 2010056906 A2 | 5/2010 |
| WO | 2010083467 A2 | 7/2010 |
| WO | 2010/132608 A2 | 11/2010 |
| WO | 2011081859 A1 | 7/2011 |
| WO | 2011097639 A2 | 8/2011 |
| WO | 2011146764 A1 | 11/2011 |
| WO | 2012068162 A2 | 5/2012 |
| WO | 2012068166 A2 | 5/2012 |
| WO | 2012135761 A1 | 10/2012 |
| WO | 2012162677 A1 | 11/2012 |
| WO | 2013026045 A1 | 2/2013 |
| WO | 2013138519 A1 | 9/2013 |
| WO | 2014006403 A1 | 1/2014 |
| WO | 2014/100392 A1 | 6/2014 |
| WO | 2014113257 A2 | 7/2014 |
| WO | 2014152005 A2 | 9/2014 |
| WO | 2014197614 A2 | 12/2014 |
| WO | 2015057766 A1 | 4/2015 |
| WO | 2016110824 A1 | 7/2016 |
| WO | 2016123278 A1 | 8/2016 |
| WO | 2016139590 A1 | 9/2016 |
| WO | 2016139597 A2 | 9/2016 |
| WO | 2016/187063 A1 | 11/2016 |
| WO | 2016176065 A1 | 11/2016 |
| WO | 2018089275 A1 | 5/2018 |
| WO | 2018089285 A1 | 5/2018 |
| WO | 2018089385 A1 | 5/2018 |
| WO | 2018191547 A1 | 10/2018 |
| WO | 2018213148 A1 | 11/2018 |
| WO | 2018218236 A1 | 11/2018 |
| WO | 2019/146026 A1 | 8/2019 |
| WO | 2019199734 A1 | 10/2019 |
| WO | 2020069395 A1 | 4/2020 |
| WO | 2020/113123 A1 | 6/2020 |
| WO | 2021050302 A1 | 3/2021 |
| WO | 2021/062023 A1 | 4/2021 |
| WO | 2021/077103 A1 | 4/2021 |
| WO | 2021081205 A1 | 4/2021 |
| WO | 2021086793 A1 | 5/2021 |
| WO | 2021/236950 A1 | 11/2021 |
| WO | 2022/031618 A1 | 2/2022 |
| WO | 2022/094141 A1 | 5/2022 |
| WO | 2022/133297 A1 | 6/2022 |
| WO | 2022-140406 A1 | 6/2022 |
| WO | 2022/140429 A1 | 6/2022 |

OTHER PUBLICATIONS

PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2021/039843 filed Jun. 30, 2021 International Search Report and Written Opinion dated Nov. 11, 2021.
PCT/US2021/044029 filed Jul. 30, 2021 International Search Report and Written Opinion dated Dec. 9, 2021.
PCT/US2020/048583 filed Aug. 28, 2020 International Search Report and Written Opinion dated Nov. 13, 2020.
PCT/US2020/052536 filed Sep. 24, 2020 International Search Report and Written Opinion dated Dec. 4, 2020.
PCT/US2020/056364 filed Oct. 19, 2020 International Search Report and Written Opinion dated Jan. 19, 2021.
PCT/US2020/056864 filed Oct. 22, 2020 International Search Report and Written Opinion dated Jan. 14, 2021.
PCT/US2020/057202 filed Oct. 23, 2020 International Search Report and Written Opinion dated Jan. 21, 2021.
PCT/US2020/057397 filed Oct. 26, 2020 International Search Report and Written Opinion dated Mar. 10, 2021.
PCT/US2021/039084 filed Jun. 25, 2021 International Search Report and Written Opinion dated Jan. 10, 2022.
U.S. Appl. No. 16/398,020, filed Apr. 29, 2019 Final Office Action dated Jan. 25, 2022.
U.S. Appl. No. 17/006,553, filed Aug. 28, 2020 Non-Final Office Action dated Mar. 16, 2022.
U.S. Appl. No. 17/077,728, filed Oct. 22, 2020 Non-Final Office Action dated Feb. 9, 2022.
U.S. Appl. No. 16/398,020, filed Apr. 29, 2019 Non-Final Office Action dated May 11, 2021.
PCT/US2021/028018 filed Apr. 19, 2021 International Preliminary Report on Patentability dated Jun. 3, 2022.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
PCT/US2021/064174 filed Dec. 17, 2021 International Search Report and Written Opinion dated May 18, 2022.
PCT/US2021/064642 filed Dec. 21, 2021 International Search Report and Written Opinion dated May 11, 2022.

\* cited by examiner

INTEGRATED ACUTE CENTRAL VENOUS CATHETER AND PERIPHERALLY INSERTED VENOUS CATHETER

PRIORITY

This application claims the benefit of priority to U.S. Provisional Application No. 62/905,363, filed Sep. 24, 2019, which is incorporated by reference in its entirety into this application.

BACKGROUND

Current methods of placing an acute central venous catheter ("ACVC") involve a multistep process of accessing a vasculature under ultrasound guidance with an introducer needle including a syringe attached to the needle hub. Removing the syringe from the introducer needle hub to observe a blood flow to ensure the needle is properly placed within the vein, and not an artery. Introducing a guidewire through the introducer needle, removing the introducer needle over the guidewire, making an incision using a scalpel, and introducing one or more dilators over the guidewire, before finally introducing a CVC catheter over the guidewire. The guidewire and/or introducer can then be removed. Often, various steps of exchanging the difference devices, such as removing the needle from the introducer needle hub, results in an accidental movement, losing the vein and aborting the attempt. Accessing the artery instead of the vein can lead to serious medical complications. Further, the clinician is required to hold the guidewire throughout the process to prevent losing the guidewire into the vasculature, and the guidewire is susceptible to contamination from exposure to unsterile surfaces. Moreover, the exchanging of multiple devices provides an increased risk of infection.

SUMMARY

Disclosed herein are integrated catheter assemblies, which in exemplary embodiments can include an acute central venous catheter with a peripherally inserted venous catheter portion at a distal end to provide rapid insertion of the device into a patient.

Briefly summarized, embodiments disclosed herein are directed to a catheter assembly and associated methods. The catheter assembly, (also termed a rapid insertion central catheter or "RICC"), comprises an elongate catheter body including a central venous catheter ("CVC") portion, and a peripheral intravenous catheter ("PIV"). The PIV portion is disposed at a distal end of the elongate body and includes a needle disposed within a lumen of the PIV portion. The PIV portion facilitates insertion of the catheter assembly, streamlining the insertion process, reducing the risk of infection, and reducing the risk of aborted attempts. Further the catheter assembly includes a guidewire with a permanently attached hub to prevent loss of the guidewire into the vasculature.

Disclosed herein is a catheter assembly for accessing a vasculature of a patient, comprising an elongate catheter body extending from a proximal end to a distal end, and defining a first lumen, the catheter body comprising, a central venous catheter ("CVC") portion, including a needle access aperture disposed through a side wall thereof, a transition portion, and a peripheral intravenous ("PIV") portion, defining a PIV lumen portion of the first lumen, and a catheter hub coupled to the proximal end of the catheter body, a peripheral intravenous ("PIV") hub, defining a PIV hub lumen, a needle defining a needle lumen, and a needle hub coupled to a proximal end thereof, the needle extending through the PIV hub lumen, the needle access aperture, and the PIV lumen portion to a point distal of the distal end of the elongate body, and a guidewire disposed in a proximal portion of the first lumen.

In some embodiments, the guidewire includes a guidewire hub permanently attached to a proximal end thereof and configured to prevent the proximal end of the guidewire from advancing distally into the first lumen. The catheter assembly further includes a syringe coupled to the needle hub and in fluid communication with the needle lumen, the syringe creating a vacuum to draw a blood flow through the needle lumen and confirm vascular access. The PIV hub includes a clip to couple the PIV hub to the catheter body. The PIV hub is configured to align a tip of the needle with the distal end of the catheter body such that a bevel of the needle is distal to the distal end of the catheter body. The PIV hub includes an anti-rotation feature that orients a bevel of the needle in a predetermined position. The anti-rotation feature includes a slot disposed in the PIV hub and a rib disposed on the needle hub, the rib and the slot oriented so that the PIV hub and the needle hub only fully engage when the bevel is oriented in an upward position. The catheter hub includes an extension leg extending proximally from a proximal end thereof, the extension leg defining an extension leg lumen in fluid communication with the first lumen, the extension leg including a connector at a proximal end thereof.

In some embodiments, the needle access aperture includes a slit valve that closes the needle access aperture when the needle is removed therefrom. The catheter body further includes a second lumen extending from the catheter hub to an outlet aperture disposed through the side wall of the CVC portion proximate a distal end thereof. The catheter hub includes a second extension leg defining a second extension leg lumen that is in fluid communication with the second lumen of the catheter body. The PIV portion defines a first diameter and the CVC portion defines a second diameter, the first diameter being less than the second diameter. The transition portion includes a tapered outer surface extending from the first diameter to the second diameter. The PIV portion includes a tip, the tip defining a tapered outer profile and defining an inner lumen diameter, the inner lumen diameter being less than an outer diameter of a shaft of the needle.

Also disclosed is a method of inserting a catheter into a vasculature of a patient, comprising, providing a catheter assembly, comprising, an elongate catheter body extending from a proximal end to a distal end, and defining a first lumen, the catheter body comprising, a central venous catheter ("CVC") portion, including a needle access aperture disposed through a side wall thereof, an transition portion, and a peripheral intravenous ("PIV") portion defining a PIV lumen portion of the first lumen, a catheter hub disposed at the proximal end of the catheter body, a peripheral intravenous ("PIV") hub coupled to the catheter body and defining a PIV hub lumen, a needle defining a needle lumen and including a needle hub coupled to the PIV hub, the needle disposed through the PIV hub lumen, the needle access aperture, the PIV lumen portion, and extending beyond the distal end of the catheter body, and a guidewire, disposed within the first lumen. Inserting the needle into the patient to access the vasculature thereof such that the distal end of the catheter body is disposed within the vasculature, observing a blood flow at the needle hub to confirm vascular access, detaching the needle hub from the PIV hub, withdrawing the needle proximally from the PIV hub, advancing the PIV portion distally into the vasculature, detaching the PIV hub from the catheter body, advancing the guidewire through the first lumen such that a distal end of the guidewire distal of the distal end of the catheter body, and advancing the catheter body over the guidewire such that a the CVC portion is disposed within the vasculature.

In some embodiments, the PIV portion includes a tip, the tip defining a tapered outer profile and defining an inner lumen diameter, the inner lumen diameter being less than an outer diameter of a shaft of the needle to secure the tip of the PIV portion thereto. The PIV portion defines a first diameter and the CVC portion defines a second diameter, the first diameter being less than the second diameter, the transition portion including a tapered outer surface extending from the first diameter to the second diameter. The PIV hub includes a clip to couple the PIV hub to the catheter body and includes an anti-rotation feature that engages the needle hub to orientate a bevel of the needle in predetermined position. The anti-rotation feature includes a slot disposed in the PIV hub and a rib disposed on the needle hub, the rib engaging the slot to orient the bevel in an upward position. The needle access aperture includes a valve that closes the needle access aperture when the needle is removed therefrom. The catheter body further includes a second lumen extending from the catheter hub to an outlet aperture disposed through a side wall of the CVC portion, the catheter hub including a second extension leg defining a second extension leg lumen that is in fluid communication with the second lumen. A distal end of the guidewire is disposed proximate the needle access aperture prior to the needle accessing the vasculature of the patient. The method further including a syringe coupled to the needle hub and in fluid communication with the needle lumen, the syringe creating a vacuum to draw a blood flow through the needle lumen and confirming vascular access.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
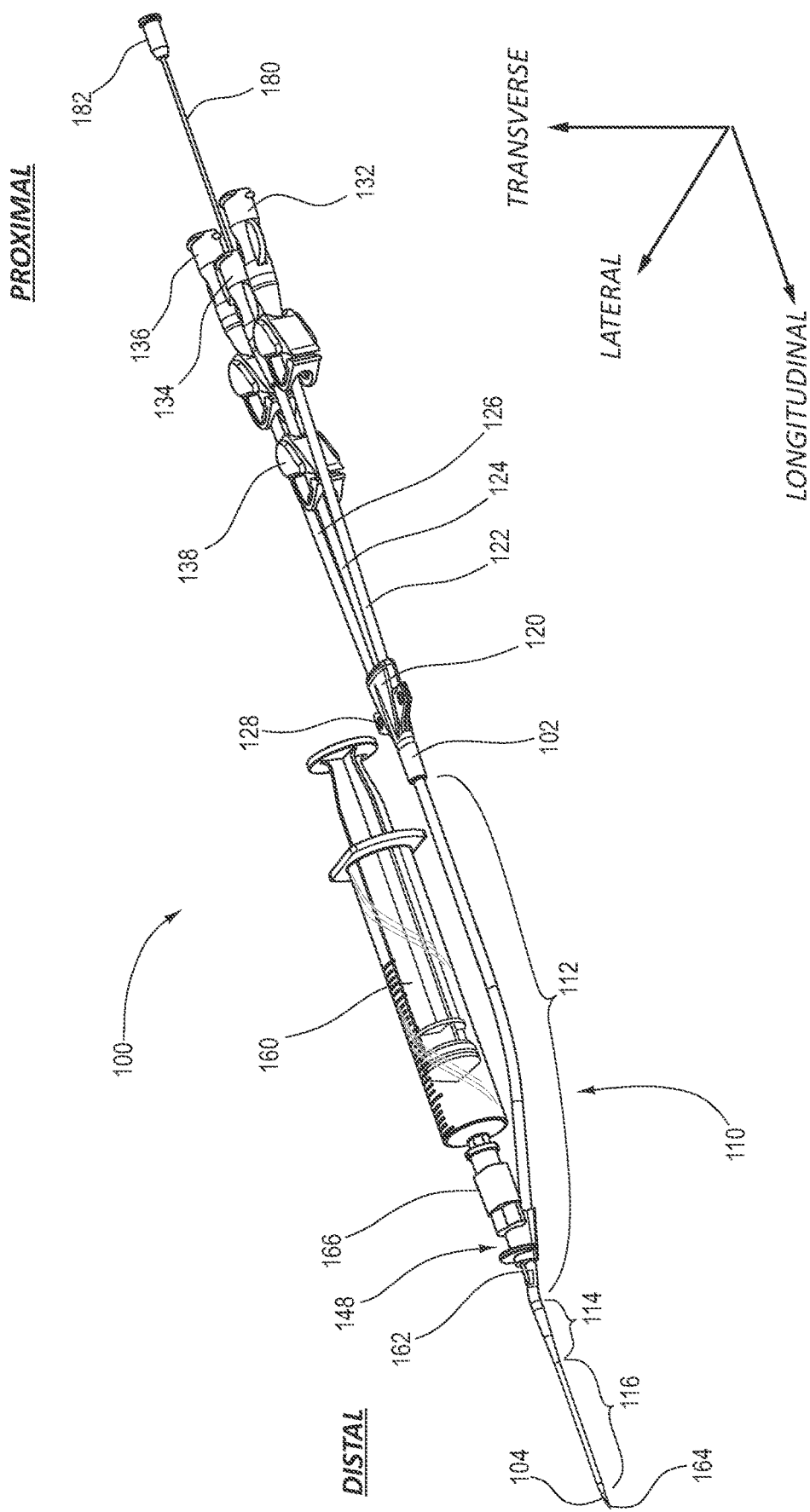
FIG. 1 illustrates a perspective view of a catheter assembly including a needle, a syringe, and a guidewire, in accordance with embodiments disclosed herein.

Reference will now be made to figures wherein like structures will be provided with like reference designations.

It is understood that the drawings are diagrammatic and schematic representations of exemplary embodiments of the present invention, and are neither limiting nor necessarily drawn to scale.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

For clarity it is to be understood that the word "proximal" refers to a direction relatively closer to a clinician using the device to be described herein, while the word "distal" refers to a direction relatively further from the clinician. For example, with respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter. Also, the words "including," "has," and "having," as used herein, including the claims, shall have the same meaning as the word "comprising."

The terms "needle" and "cannula" can be used herein interchangeably to refer to a member having a sharpened or beveled end for insertion into an injection site on a subject. In one embodiment, the needle can be a thin hollow tubular member. "Axial" means along or parallel to the longitudinal axis of the needle and the "radial" direction is a direction perpendicular to the axial direction. The forward direction is the direction toward the distal end of the device. Unless defined otherwise, all technical and scientific terms used herein have the same meaning as commonly understood by those of ordinary skill in the art.

Embodiments disclosed herein are directed to a catheter assembly 100 including features that provide a streamlined insertion operation and a reduced risk of medical complications. In reference to FIGS. 1-2, a catheter assembly 100 for accessing a vasculature of a patient for the introduction of fluids, medicaments, or the like, is disclosed. As shown in FIG. 1, the catheter assembly 100 generally includes an elongate catheter body 110 extending from a proximal end 102 to a distal end 104, a catheter hub 120 disposed at the proximal end 102, one or more extension legs, e.g. extension legs 122, 124, 126, a guidewire 180, a needle 162, a syringe 160, and a PIV hub 148. The elongate catheter body 110 defines one or more lumens extending from the proximal end 102 to a distal end 104 for the administration or aspiration of fluids, or the introduction of elongate medical devices. For example, the exemplary embodiment shown in FIG. 1 includes a triple lumen embodiment, although catheters with greater or fewer lumens are contemplated. Embodiments of similar catheter assembly configurations, including various lumen, needle, and guidewire configurations, as well as associated methods, can be found in U.S. Pat. No. 10,376,675, which is herein incorporated by reference in its entirety.

A catheter hub 120 is disposed at the proximal end 102 of the elongate catheter body 110 and provides one or more openings that communicate respectively with the one or more lumens of the elongate body 110. The catheter hub 120 further includes various stabilization features 128 for securing the hub to various catheter stabilization devices and, in turn, securing the catheter 110, to the patient. The stabilization features 128 can include various wings, tabs, holes, abutments, collars, and the like, or combinations thereof.

In an embodiment, the catheter hub 120 includes one or more extension legs, for example extension legs 122, 124, 126. Each extension leg defines an extension leg lumen that is in fluid communication with a lumen of the catheter body 110. Each extension leg also includes a connector, e.g. connectors 132, 134, 136, disposed at a proximal end thereof to provide fluid communication between the extension leg lumen and various fluid lines, syringes, or similar devices for the introduction of fluids, medicaments, or the like to the patient by way of the catheter 110. The connectors 132, 134, 136 can include luer locks, spin nuts, or the like.

In an embodiment, a lumen of the catheter body 110 can be configured to receive an elongate medical device such as a guidewire, stylet, trocar, or the like, or combinations thereof. As shown in FIG. 1, guidewire 180 is disposed through connector 134, extension leg 124, and catheter hub 120, and into a lumen of the catheter body 110. The guidewire 180 includes a guidewire hub 182 permanently attached to a proximal end of the guidewire 180. In an embodiment, the guidewire hub 182 includes locking features to engage connector 134 and secure the guidewire within the catheter 100. As shown, the guidewire hub 182 includes a substantially cylindrical shape, although it will be appreciated that the guidewire hub 182 can include other shapes, such as cuboid, spherical, or the like, that are designed to prevent a proximal end of the guidewire entering the lumen of the catheter 110. Optionally one or more of the extension legs 122, 124, 126 includes a clamp 138 for selectively inhibiting a fluid flow therethrough, or selectively inhibiting the movement of guidewire 180 disposed therein, or combinations thereof. The guidewire 180 can be solid, hollow, or wire-like, and formed of stainless steel, nitinol, alloys, plastic, polymer, or similar suitable material.

Figure 2:
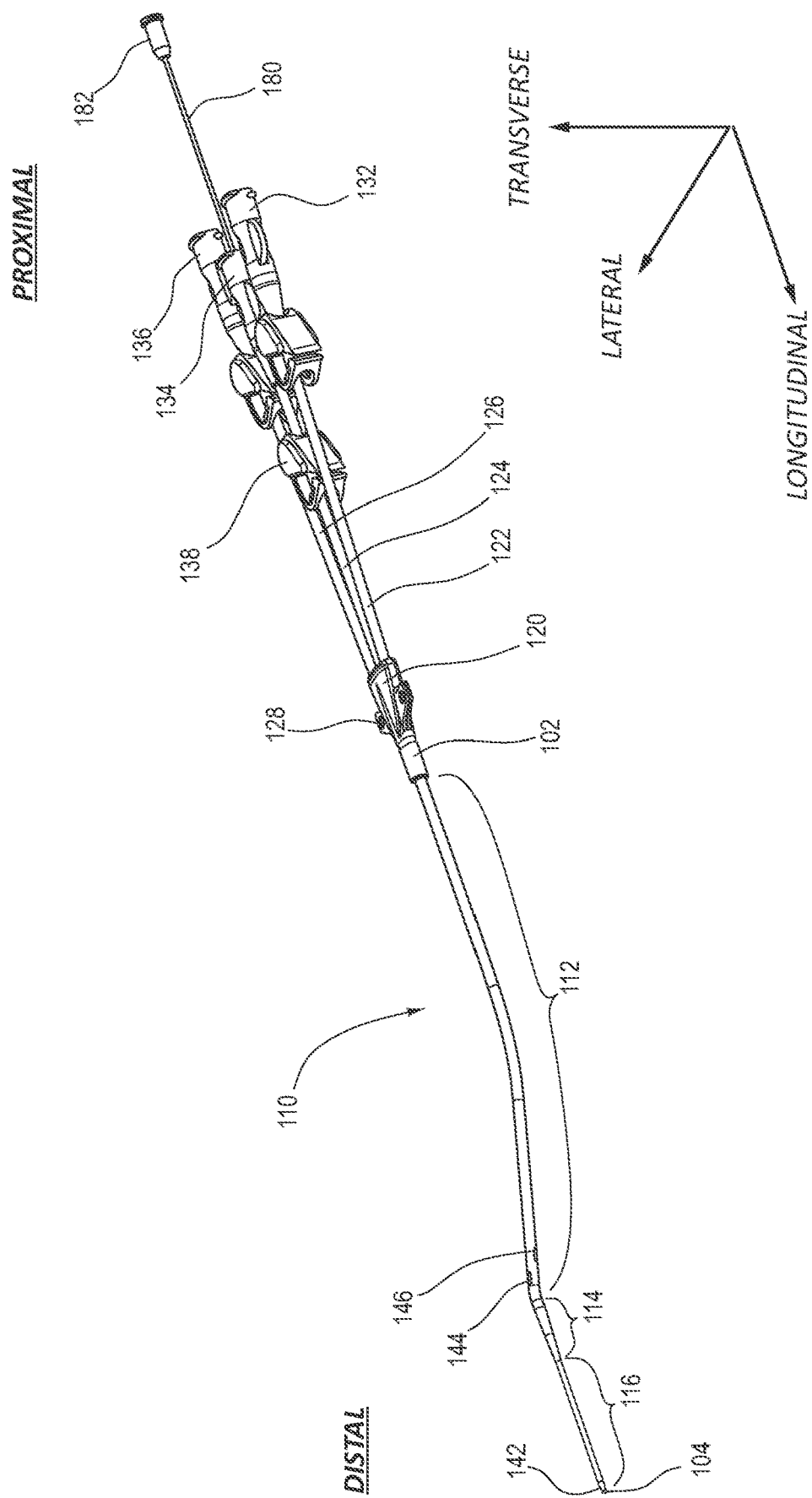
FIG. 2 illustrates a perspective view of the catheter shown in FIG. 1, in accordance with embodiments disclosed herein.

The elongate catheter body 110 extends along a longitudinal axis from a proximal end 102 to a distal end 104. The elongate body 110 includes a central venous catheter ("CVC") portion 112, a transition portion 114, and a peripheral intravenous ("PIV") portion 116. The elongate body 110 can be formed of a plastic, polymer, silicone rubber, or similar suitable material, or combinations thereof, that is flexible and biocompatible. To note, as shown in FIG. 2, the elongate body 110 is deflected from the longitudinal axis, however, this is for illustration purposes. The catheter 110, or portions thereof, can further include various reinforcements to maintain the shape of the catheter 100 and/or patency of the lumen(s).

The CVC portion 112 extends from a distal end of the catheter hub 120 to a proximal end of the transition portion 114. The transition portion 114 extends from the distal end of the CVC portion 112 to a proximal end of the PIV portion 116. The PIV portion 116 extends from the distal end of the transition portion 114 to a tapered peripheral intravenous catheter tip 142. In an embodiment, the PIV portion 116 extends between 1 cm and 20 cm, with a preferred embodiment extending 7 cm. However, it will be appreciated that the PIV portion 116 can vary in length beyond these measurements and fall within the scope of the present invention. It will also be appreciated that the relative lengths of the CVC portion 112, transition portion 114, and PIV portion 116 can also vary and still remain within the scope of the present invention.

In an embodiment, the CVC portion 112 and the PIV portion 116 define different structural and mechanical properties. The CVC portion 112 defines a relatively larger diameter, and includes one or more lumen, as described in more detail herein. The material forming the CVC portion 112 includes a relatively softer durometer of approximately 93 A Shore. This allows the CVC portion 112 to navigate tortuous vasculature of the patient.

The PIV portion 116 defines a relatively smaller diameter than the CVC portion 112, and typically defines only a single lumen. However, it will be appreciated that embodiments of the PIV portion 116 defining one or more lumen are also contemplated. The material forming the PIV portion 116 is relatively harder than then CVC portion 112, with a durometer of approximately 72 D Shore. The PIV portion 116 also defines a greater columnar strength and a greater hoop strength than the CVC portion 112, and in an embodiment, includes reinforcements disposed within a wall of the PIV portion 116 to improve columnar and hoop strength. This allows the PIV portion 116 to withstand greater compressive forces along a longitudinal axis, such as those sustained while being urged distally and inserted through a skin surface and subcutaneous tissues of the patient. The PIV portion 116 can then maintain the overall shape of the PIV portion 116 and the patency of any lumen defined therein.

The transition portion 114 provides a transition between the different structural and mechanical properties of the CVC portion 112 and the PIV portion 116. The transition portion 116 includes a taper to provide a smooth outer profile between the relatively smaller diameter of the PIV portion 116 and the relatively larger diameter of the CVC portion 112. Advantageously, the transition portion 114 provides a self-dilating feature as the catheter body 110 is advanced into the patient, as described in more detail herein.

In an embodiment, the PIV portion 116, transition portion 114, CVC portion 112, or combinations thereof include a lubricious coating. As described herein, the CVC portion 112, transition portion 114, and the PIV portion 116 of the catheter body 110 are provided as a single structure. It will be appreciated that, in an embodiment, the CVC portion 112, transition portion 114, and the PIV portion 116, or combinations thereof can also be provided as separate structures and connected thereto using various temporary or permanent couplings. For example, the one or more portions 112, 114, 116 of the catheter body 110 can be provided as separate structures and bonded, welded, fused, or adhered together. Methods of forming catheters, such as the catheters described herein with one or more portions, are disclosed in U.S. Provisional Application No. 62/898,408, filed Sep. 10, 2019, which is incorporated in its entirety into this application.

Figure 3:
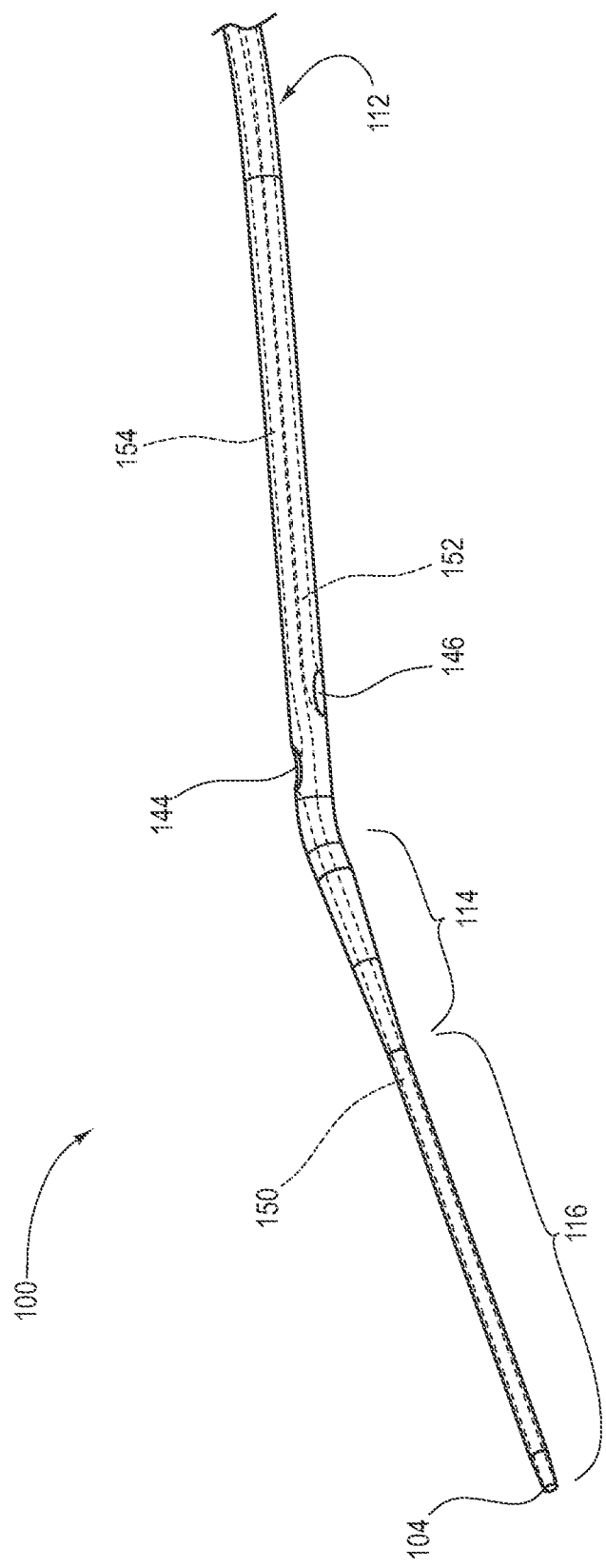
FIG. 3 illustrates a close up view of a distal portion of the catheter of FIG. 2, in accordance with embodiments disclosed herein.

FIG. 3 shows a close up view of the PIV portion 116, transition portion 114 and the distal end of the CVC portion 112. A distal end of the CVC portion 112 includes a needle access aperture 144 and one or more outlet apertures, for example a first outlet aperture 146, disposed through a side wall thereof. As described herein, the elongate body 110 includes one or more lumens. A first lumen 152 extends from a first connector 132 to a first outlet aperture 146, disposed through a side wall of the CVC portion 112. A second lumen 154 extends from a second connector 134 to an opening at the distal end 104 of the elongate body 110. A third lumen (not shown) extends from a third connector 136 to a second outlet aperture (not shown) disposed through a side wall of the CVC portion 112, opposite the first outlet aperture 146. In an embodiment, the first lumen 152 and third lumen (not shown) also extend through the PIV portion 116, to a distal end 104.

In an embodiment, the guidewire 180 is disposed within the second lumen 154 such that a distal end of the guidewire 180 is disposed proximate a distal end of the CVC portion 112, for example adjacent the needle access aperture 144. Advantageously this allows rapid deployment of the guidewire since it is provided preloaded within the catheter body 110 and is already proximate to a distal end 104 of the catheter 110. In an embodiment, the outer diameter of the guidewire 180 is substantially the same as the inner diameter of the second lumen 154 such that any fluid flowing proximally through the lumen 154 is substantially blocked by the guidewire 180 disposed therein. In an embodiment, the guidewire 180 extends through the CVC portion 112, transition portion 114, and into a PIV lumen portion 150 of the second lumen 154. In an embodiment, when the guidewire hub 182 engages connector 134, the guidewire 180 extends to the distal end 104 of the catheter 110. In an embodiment, the guidewire 180 extends distally beyond the distal end 104 of the catheter 110. In an embodiment, the guidewire 180 extends 15 cm beyond the distal end 104 of the catheter 110. In an embodiment, the guidewire 180 extends sufficiently beyond the distal end 104 of the catheter 110 to reach the lower ⅓ of the superior vena cava ("SVC"). In an embodiment, a clamp 138 can selectively secure the guidewire 180 in position.

Figure 4:
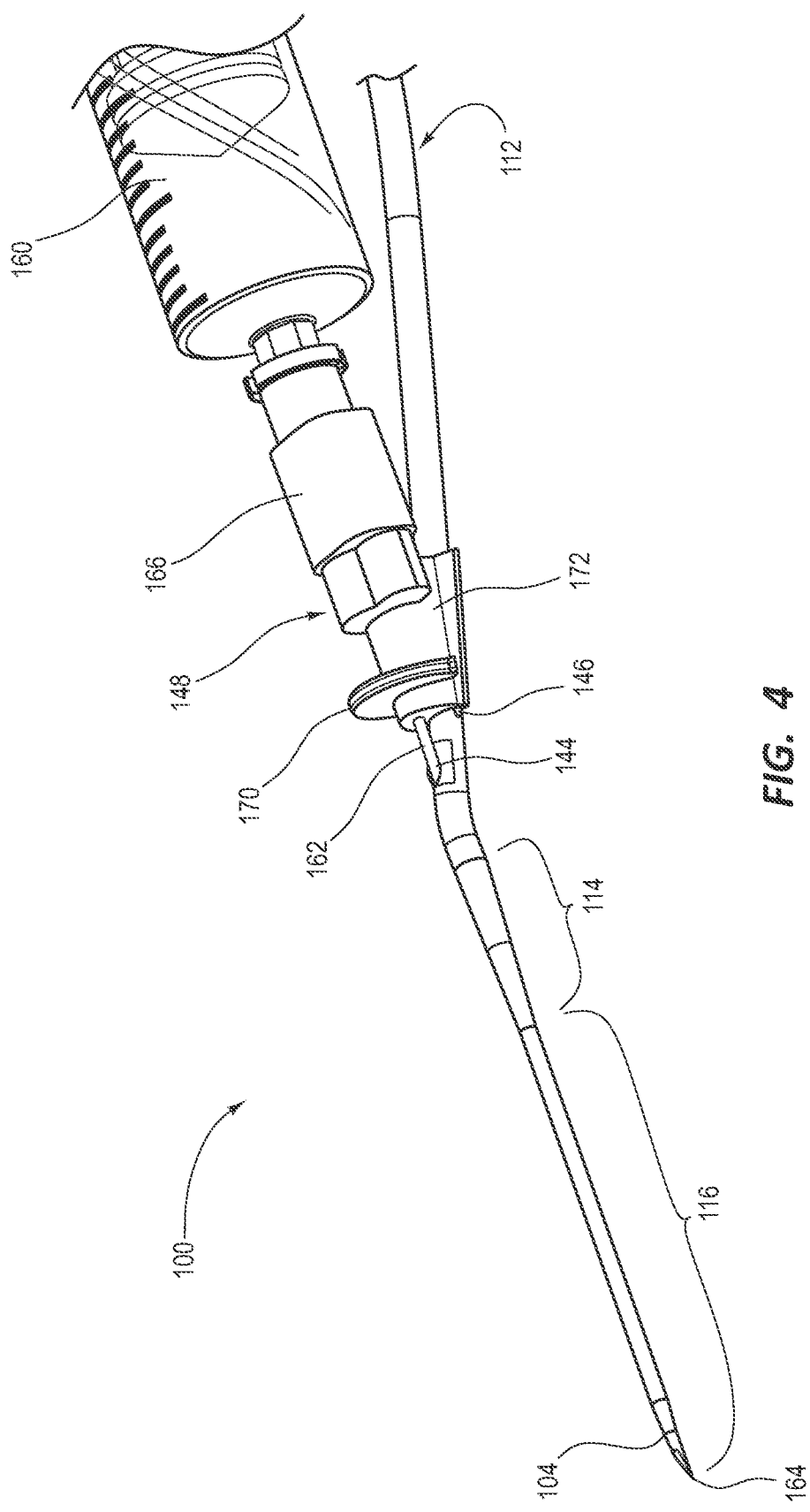
FIG. 4 illustrates a close up view of distal portion of the catheter assembly of FIG. 1, in accordance with embodiments disclosed herein.

As shown in FIGS. 1 and 4, the catheter assembly 100 includes a syringe 160 and a needle 162. A proximal end of the needle hub 166 includes a connector to allow various medical lines, syringes, and the like, e.g. syringe 160, to fluidly communicate with a lumen of the needle 162. The connector between the hub 166 and the syringe 160 can be a luer lock, spin nut, or similar suitable connector. In an embodiment, the needle 162 and needle hub 166 includes a valve apparatus to prevent a flow through the needle when the syringe 160 is not connected thereto. In an embodiment, the needle 162 and needle hub 166 includes a blood flashback indicator apparatus to indicate when the needle tip 164 has accessed a vasculature of the patient. In an embodiment, the syringe 160 or similar device, can induce a vacuum to draw a blood flow to confirm the needle tip 164 has accessed a vasculature correctly. In an embodiment, the syringe 160 can be selectively detached from the needle 162 to observe a blood flow to confirm the needle tip 164 has accessed a vasculature correctly. For example if a blood flow is substantially steady and dark red, the clinician can confirm venous access and continue with the procedure. However, if the blood flow is pulsating and bright red, the clinician can confirm arterial access.

The needle 162 extends through the needle access aperture 144, into the PIV lumen portion 150 of the second lumen 154, such that a needle tip 164 extends distally beyond a distal end 104 of the catheter body 110. In an embodiment, the needle access aperture 144 includes, a slit, a U-shaped slit, circular or elliptical aperture, or similar structure. In an embodiment, the needle access aperture 144 includes a needle penetrable material such a silicone, or the like, that allows the needle 162 to penetrate the aperture 144 but prevents any fluid from escaping once the needle 162 is removed. In an embodiment, the needle access aperture 144 includes a valve that allows access to the needle 162 and closes the aperture 144 when the needle 162 is removed.

As shown in FIG. 4, in an embodiment, a PIV hub 148 is coupled with elongate body 110 and defines a PIV hub lumen that aligns with the needle access aperture 144 and the PIV lumen portion 150, substantially parallel to a longitudinal axis. The PIV hub 148 facilitates alignment of the needle 162 with the needle access aperture 144 and the PIV lumen portion 150. In an embodiment, the PIV hub 148 includes an anti-rotational feature that aligns a bevel 174 of the needle 162 in a predetermined position, e.g. an upward position, downward position, or the like. In an embodiment, the proximal end of the PIV hub 148 includes various detents, abutments, guides, and the like, or combinations thereof that engage similar structures on a needle hub 166 to align a bevel 174 of the needle 162 in an upward position. In an embodiment, the needle hub 166 includes a rib that engages a slot disposed in the PIV hub 148. The slot and rib are oriented such that the PIV hub 148 and the needle hub 166 only fully engage when the bevel of the needle 162 is oriented correctly, in an upwards orientation to facilitate skin puncture.

In an embodiment, the PIV hub 148 further includes a tab 170. A clinician can use the tab 170 to stabilize the PIV hub 148 when separating the needle hub 166 therefrom. In an embodiment, the PIV hub 148 includes a clip 172 that secures to the PIV hub 148 to an adjacent portion of the elongate body 110, i.e. a distal end of the CVC portion 112. The clip 172 stabilizes the PIV hub 148, and needle 162 coupled thereto, and prevents the needle 162 from being accidentally withdrawn from the needle access aperture 144. The clip 172 also allows the PIV hub 148 to be selectively removed from the device 100. Further, the PIV hub 148 is coupled to the CVC portion 112 at a position such that a lie distance between the needle tip 164 and the distal end 104 of the catheter body 110 is correctly aligned, as described in more detail below. In an embodiment, the catheter body 110 includes various markings, detents, protrusions, or combinations thereof, to ensure the PIV hub 148 is correctly situated on the catheter body 110, relative to the distal end 104.

Figure 5A:
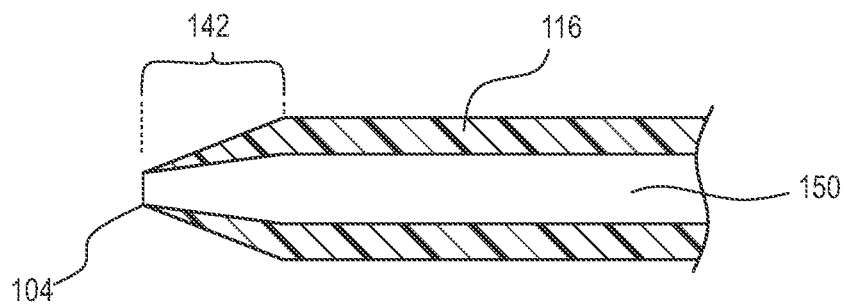
FIGS. 5A-5C illustrates various details of the distal end of the catheter assembly of FIG. 1, in accordance with embodiments disclosed herein.
Figure 5B:
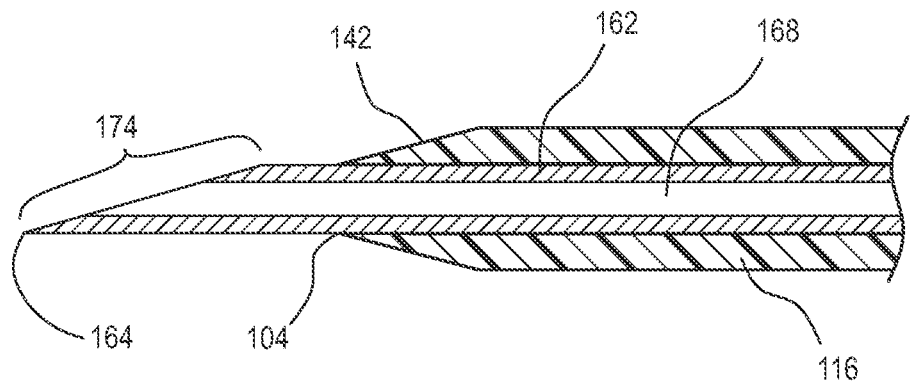
Figure 5C:
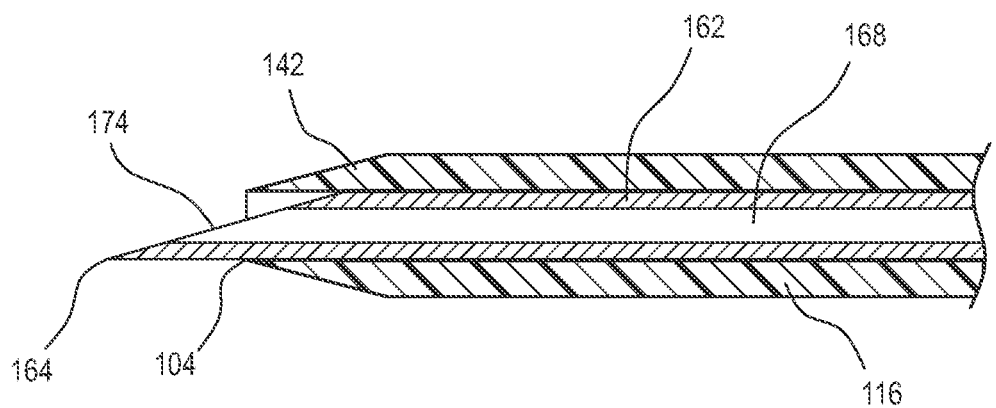

FIGS. 5A-5C show a close up cross-sectional view of the distal end of the PIV portion 116. FIG. 5A shows the distal end of the PIV portion 116 without the needle 162 disposed therein. The tip 142 of the PIV portion 116, defines a tapered outer profile, gradually reducing from the relatively larger diameter of the PIV portion 116 to the relatively smaller diameter of the distal end 104. The lumen diameter of the tip portion 142 is also tapered, gradually reducing from the relatively larger diameter of the PIV lumen portion 150 to the relatively smaller diameter of the lumen of the distal end 104.

FIG. 5B shows a close up cross-sectional view of the distal end of the PIV portion 116 with the needle 162 disposed therein. The outer diameter of the needle 162 is sized to fit snuggly within the PIV lumen portion 150. The inner diameter of the lumen at the distal end 104, is sized to be relatively smaller than the outer diameter of the needle 162. Accordingly, when the needle 162 is positioned through the distal end 104, such that the entire bevel 174 of the needle 162 extends distally beyond the distal end 104 of the catheter 110, the distal end 104 stretches to fit tightly about the outer diameter of the shaft of the needle 162. As described herein, the PIV hub 148 is positioned to ensure a correct lie distance between the needle tip 164 and the distal end 104, for example as shown in FIG. 5B.

In contrast, as shown in FIG. 5C, when the lie distance between the needle tip 164 and the distal end 104 is misaligned, a portion of the bevel 174 of the needle 162 remains proximal of the distal end 104. As such, if the catheter assembly 100 is advanced into a patient, tissue and fluid can be forced between the inner wall of the lumen 150 the needle 162 disrupting the smooth advancement of the catheter assembly 100.

In an exemplary method of use, a catheter assembly 100 is provided as described herein, in a preassembled form. It will be appreciated, however, that components of the catheter assembly 100 can also be provided as a kit, in an unassembled form, or provided separately, and can be assembled by the clinician prior to use. A clinician accesses a vasculature of a patient using the needle tip 164. A proximal blood flow through the needle lumen 168 can be observed at the needle hub 166 to ensure correct vascular access. For example, a dark red, relatively steady flow indicates venous access and the procedure can continue. However, a bright red, pulsating flow indicates arterial access and the procedure can be aborted. It is important to note that arterial access using traditional CVC placement procedures can result in serious medical complications. However, arterial access using the relatively smaller diameter needle 162 and PIV portion 116 can be resolved by simply applying pressure. In an embodiment, a syringe 160 or similar device coupled to the needle hub 166 can induce a vacuum to draw a blood flow proximally through the needle lumen 168. This can be used to confirm correct vascular access where the blood pressure alone is insufficient to advance a blood flow proximally to a needle hub 166. In an embodiment, the syringe 160 can also contain any blood flowing from the needle hub 166. In an embodiment, the needle hub 166 can further include a valve that prevents a blood flow when the syringe 160 is detached.

Once vascular access has been confirmed, the clinician can detach the catheter 110 from the needle 162/syringe 160 assembly by stabilizing the PIV hub 148 with a digit and detaching the needle hub 166 in a proximal direction. The PIV push off tab 170 can provide a surface with which the clinician can stabilize the PIV hub 148. Once detached, the PIV portion 116 can be advanced distally, off of the needle 162 and into the vasculature of the patient. The clinician can grasp the PIV hub 148 to advance the PIV portion 116 and the needle 162/syringe 160 assembly withdrawn proximally and discarded. In an embodiment, once the needle 162 has been removed from the catheter body 110, a valve or similar structure closes the needle access aperture 144 to prevent a blood flow therethrough. The PIV hub 148 can then be detached from the catheter body 110 and discarded.

To note, the tapered tip 142 of the PIV portion 116 fits tightly about the shaft of the needle 162, and is secured thereto. This provides a smooth outer profile as the needle 162/PIV tip 142 assembly penetrates the skin surface and accesses the vasculature. With the needle 162 removed and the PIV tip 142 disposed within the vasculature, the guidewire 180 can be advanced through the lumen 150 of the PIV portion 116 and into the vasculature. The PIV portion 116 provides sufficient columnar and hoop strength to be urged distally over the guidewire 180, into the vasculature, without kinking, and maintains the patency of the PIV lumen 150. The PIV portion 116 also includes a relatively smaller diameter, and optionally a lubricious coating, to facilitate distal advancement into the vasculature.

With the needle 162 removed, the guidewire 180 disposed within lumen 154 can then be advanced through the PIV lumen portion 150 and beyond a distal end 104 to enter the vasculature of the patient. The guidewire can be advanced to a target location such as the lower ⅓ of the superior vena cava. It will be appreciated that the guidewire hub 182, permanently attached to the guidewire 180, prevents the guidewire 182 from advancing too far into the vasculature and prevents accidental loss of the guidewire 180 into the vasculature, even if the clinician accidently releases the guidewire.

To note, the guidewire 180 is provided preloaded within the lumen 154 prior to the start of the procedure. The distal end of the guidewire 180, disposed proximate the needle access aperture 144, allows for rapid deployment of the guidewire 180 once the needle 162 has been removed. The distal end of the guidewire 180 needs only to travel substantially the distance of the PIV portion 116 to access the vasculature. By contrast, traditional methods of placing a CVC catheter would require feeding the guidewire into a proximal end of the CVC catheter and advancing along the entire length of the CVC catheter to enter the vasculature, costing extra time and providing increased risk of infection.

With the guidewire in place, the catheter 110 can then be advanced over the guidewire 180. As the transition portion 114 passes over the guidewire 180 and through the insertion site, the tapered outer profile provides an automatic dilation of the insertion site from the diameter of the PIV portion 116 to the relatively larger diameter of the CVC portion 112. In an embodiment, the transition portion 114, the CVC portion 112, or combinations thereof can include a lubricious coating, disposed thereon, to facilitate access.

The catheter body 110 is then advanced over the guidewire 180, until the outlet apertures, e.g. outlet aperture 146 is disposed at a desired location. The catheter hub 120 is then secured proximate the insertion site, and the guidewire 180 can be removed. Various medial lines can then be connected to the connector 132, 134, 136 to introduce fluids, medicaments, and the like to the vasculature by way of outlet apertures, e.g. outlet aperture 146. In an embodiment, the guidewire lumen 154 can be used to introduce fluids by way of the needle access aperture 144, the opening at the distal end 104, or combinations thereof.

Advantageously, the catheter assembly 100 provides the ease of placement, typically associated with PIV catheters, with the functionality of a CVC catheter. Traditional methods of placing CVC catheters involves a complex process involving a surgical incision to access the vasculature and an increased risk of significant medical complications and infection. By contrast, placement of the catheter assembly 100 requires a relatively small puncture site and fewer devices are introduced and removed. This expedites the procedure and reduces the risk of medical complications and infection.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter assembly for accessing a vasculature of a patient, comprising:
   an elongate catheter body extending from a proximal end to a distal end, and defining a first lumen, the catheter body comprising:
      a central venous catheter ("CVC") portion, including a needle access aperture disposed through a side wall thereof;
      a transition portion; and
      a peripheral intravenous ("PIV") portion, defining a PIV lumen portion of the first lumen; and
   a catheter hub coupled to the proximal end of the catheter body;
   a peripheral intravenous ("PIV") hub, defining a PIV hub lumen;
   a needle, defining a needle lumen, and a needle hub coupled to a proximal end thereof, the needle extending through the PIV hub lumen, the needle access aperture, and the PIV lumen portion to a point distal of the distal end of the catheter body; and
   a guidewire disposed in a proximal portion of the first lumen.

2. The catheter assembly according to claim 1, wherein the guidewire includes a guidewire hub permanently attached to a proximal end thereof and configured to prevent the proximal end of the guidewire from advancing distally into the first lumen.

3. The catheter assembly according to claim 1, further including a syringe coupled to the needle hub and in fluid communication with the needle lumen, the syringe creating a vacuum to draw a blood flow through the needle lumen and confirm vascular access.

4. The catheter assembly according to claim 1, wherein the PIV hub includes a clip to couple the PIV hub to the catheter body.

5. The catheter assembly according to claim 1, wherein the PIV hub is configured to align a tip of the needle with the distal end of the catheter body such that a bevel of the needle is distal to the distal end of the catheter body.

6. The catheter assembly according to claim 1, wherein the PIV hub includes an anti-rotation feature that orients a bevel of the needle in a predetermined position.

7. The catheter assembly according to claim 6, wherein the anti-rotation feature includes a slot disposed in the PIV hub and a rib disposed on the needle hub, the rib and the slot oriented so that the PIV hub and the needle hub only fully engage when the bevel is oriented in an upward position.

8. The catheter assembly according to claim 1, wherein the catheter hub includes an extension leg extending proximally from a proximal end thereof, the extension leg defining an extension leg lumen in fluid communication with the first lumen, the extension leg including a connector at a proximal end thereof.

9. The catheter assembly according to claim 1, wherein the needle access aperture includes a slit valve that closes the needle access aperture when the needle is removed therefrom.

10. The catheter assembly according to claim 1, wherein the catheter body further includes a second lumen extending from the catheter hub to an outlet aperture disposed through the side wall of the CVC portion proximate a distal end thereof.

11. The catheter assembly according to claim 10, wherein the catheter hub includes a second extension leg defining a second extension leg lumen that is in fluid communication with the second lumen of the catheter body.

12. The catheter assembly according to claim 1, wherein the PIV portion defines a first diameter and the CVC portion defines a second diameter, the first diameter being less than the second diameter.

13. The catheter assembly according to claim 12, wherein the transition portion includes a tapered outer surface extending from the first diameter to the second diameter.

14. The catheter assembly according to claim 1, wherein the PIV portion includes a tip, the tip defining a tapered outer profile and defining an inner lumen diameter, the inner lumen diameter being less than an outer diameter of a shaft of the needle prior to an insertion of the shaft of the needle through the tip.

15. A method of inserting a catheter into a vasculature of a patient, comprising:
   providing a catheter assembly, comprising:
      an elongate catheter body extending from a proximal end to a distal end, and defining a first lumen, the catheter body comprising:
         a central venous catheter ("CVC") portion, including a needle access aperture disposed through a side wall thereof;
         a transition portion; and
         a peripheral intravenous ("PIV") portion defining a PIV lumen portion of the first lumen;
      a catheter hub disposed at the proximal end of the catheter body;
      a peripheral intravenous ("PIV") hub coupled to the catheter body and defining a PIV hub lumen;
      a needle defining a needle lumen and including a needle hub coupled to the PIV hub, the needle disposed through the PIV hub lumen, the needle access aperture, the PIV lumen portion, and extending beyond the distal end of the catheter body; and
      a guidewire, disposed within the first lumen;
   inserting the needle into the patient to access the vasculature thereof such that the distal end of the catheter body is disposed within the vasculature;
   observing a blood flow at the needle hub to confirm vascular access;
   detaching the needle hub from the PIV hub;
   withdrawing the needle proximally from the PIV hub;
   advancing the PIV portion distally into the vasculature;
   detaching the PIV hub from the catheter body;
   advancing the guidewire through the first lumen such that a distal end of the guidewire is distal of the distal end of the catheter body; and advancing the catheter body over the guidewire such that the CVC portion is disposed within the vasculature.

16. The method according to claim 15, wherein the PIV portion includes a tip, the tip defining a tapered outer profile and defining an inner lumen diameter, the inner lumen diameter being less than an outer diameter of a shaft of the needle prior to an insertion of the shaft of the needle through the tip to secure the tip of the PIV portion thereto.

17. The method according to claim 15, wherein the PIV portion defines a first diameter and the CVC portion defines a second diameter, the first diameter being less than the second diameter, the transition portion including a tapered outer surface extending from the first diameter to the second diameter.

18. The method according to claim 15, wherein the PIV hub includes a clip to couple the PIV hub to the catheter body and includes an anti-rotation feature that engages the needle hub to orientate a bevel of the needle in a predetermined position.

19. The method according to claim 18, wherein the anti-rotation feature includes a slot disposed in the PIV hub and a rib disposed on the needle hub, the rib engaging the slot to orient the bevel in an upward position.

20. The method according to claim 15, wherein the needle access aperture includes a valve that closes the needle access aperture when the needle is removed therefrom.

21. The method according to claim 15, wherein the catheter body further includes a second lumen extending from the catheter hub to an outlet aperture disposed through a side wall of the CVC portion, the catheter hub including a second extension leg defining a second extension leg lumen that is in fluid communication with the second lumen.

22. The method according to claim 15, wherein a distal end of the guidewire is disposed proximate the needle access aperture prior to the needle accessing the vasculature of the patient.

23. The method according to claim 15, further including a syringe coupled to the needle hub and in fluid communication with the needle lumen, the syringe creating a vacuum to draw a blood flow through the needle lumen and confirming vascular access.

* * * * *